(12) United States Patent
Noh et al.

(10) Patent No.: US 6,797,703 B1
(45) Date of Patent: Sep. 28, 2004

(54) GENE THERAPY USING TGF-β

(75) Inventors: Moon Jong Noh, Kyunggi-Do (KR);
Kyoung Ae Kang, Kyunggi-Do (KR);
Kwan Hee Lee, Seoul (KR)

(73) Assignee: Tissuegene, Inc., Gaithersburg, MD (US)

( * ) Notice: Subject to any disclaimer, the term of this patent is extended or adjusted under 35 U.S.C. 154(b) by 0 days.

(21) Appl. No.: 09/702,718

(22) Filed: Nov. 1, 2000

Related U.S. Application Data

(63) Continuation-in-part of application No. 09/345,415, filed on Jun. 30, 1999, now Pat. No. 6,315,992.

(51) Int. Cl.[7] .......................... A61K 35/00; A61K 48/00
(52) U.S. Cl. ........................................ 514/44; 424/93.2
(58) Field of Search ............................ 424/93.21, 93.2, 424/93.1; 514/44

(56) References Cited

U.S. PATENT DOCUMENTS 5,842,477 A * 12/1998 Naughton et al. .......... 128/898
6,315,992 B1 * 11/2001 Noh et al. ................ 424/93.21

OTHER PUBLICATIONS

Verma et al., Gene therapy–promises, problems and prospects, 1997, NATURE, vol. 389, pp. 239–242.*
Song et al., Plasmid DNA encoding transforming growth factor–Beta 1 suppresses chronic disease in a streptococcal cell wall–induced arthritis model, vol. 101, pp. 2615–2621.*
Fox et al., Biological therapies: A novel approach to the treatment of autoimmune disease, 1995, The American Journal of Medicine, vol. 99, pp. 82–88.*
Pelletier et al., In vivo suppression of early experimental osteoarthritis by interleukin–1 receptor antagonist using gene therapy, 1997, Athritis & Rheumatism, vol. 40, pp. 1012–1019.*
Crystal, Transfer of genes to humans: Early lessons and obstacles to success, 1995, SCIENCE, vol. 270, pp. 404–410.*
Deonarain, Ligand–targeted receptor–mediated vectors for gene delivery, 1998, Exp. Opin. Ther. Patents, vol. 8, pp. 53–69.*
Miller et al., Targeted vectors for gene therapy, 1995, FASEB, vol. 9, pp. 190–199.*
Chernajovsky et al., Pathogenic lymphoid cells engineered to express TGF Beta 1 ameliorate disease in a collagen–induced arthritis model, 1997, Gene Therapy, vol. 4, pp. 553–559.*
Van Beuningen et al., Differential effects of local application of BMP–2 or TGF–beta 1 on both articular cartilage composition and osteophyte formation, 1998, Osteoarthritis and Cartilage, vol. 6, pp. 306–317.*
Ikeda et al., adenovirus mediated gene delivery to the joints of guinea pigs, 1998, The Journal of Rheumatology, vol. 25, pp. 1666–1673.*

* cited by examiner

Primary Examiner—Michael C. Wilson
(74) Attorney, Agent, or Firm—JHK Law; Joseph Hyosuk Kim

(57) ABSTRACT

The subject invention is related to a cell-mediated gene therapy treatment for orthopedic disease using a member belonging to the transforming growth factory-β (TGF-β) superfamily. TGF-β gene therapy as a new treatment method for degenerative arthritis is demonstrated. After transfection of TGF-β cDNA expression vectors into fibroblasts (NIH 3T3-TGF-β1), the cells were injected into rabbit achilles tendon and knee joints with artificially-made cartilage defects. Intratendinous injections were performed to determine the optimal concentration for in vivo expression. Partially defected cartilage model was made to simulate degenerative arthritis of the knee joint. The partial cartilage defect treated with the cell-mediated gene therapy procedure was covered by newly formed hyaline cartilage which indicates that the cells survived and stimulated matrix formation in this area. Completely denuded cartilage areas were covered by fibrous collagen.

11 Claims, 12 Drawing Sheets

Fig 7
Control cells
TGF-β1-transfected cells
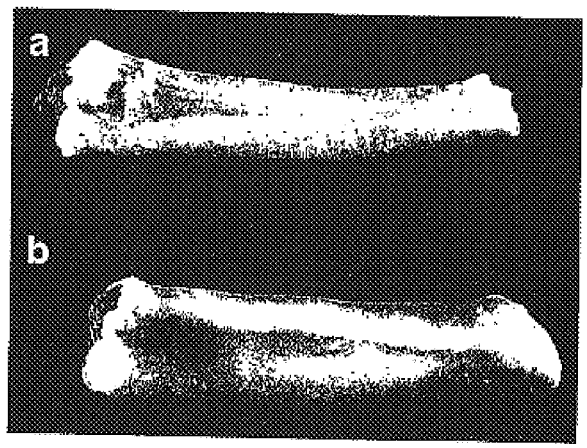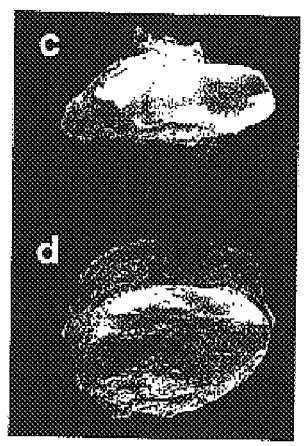

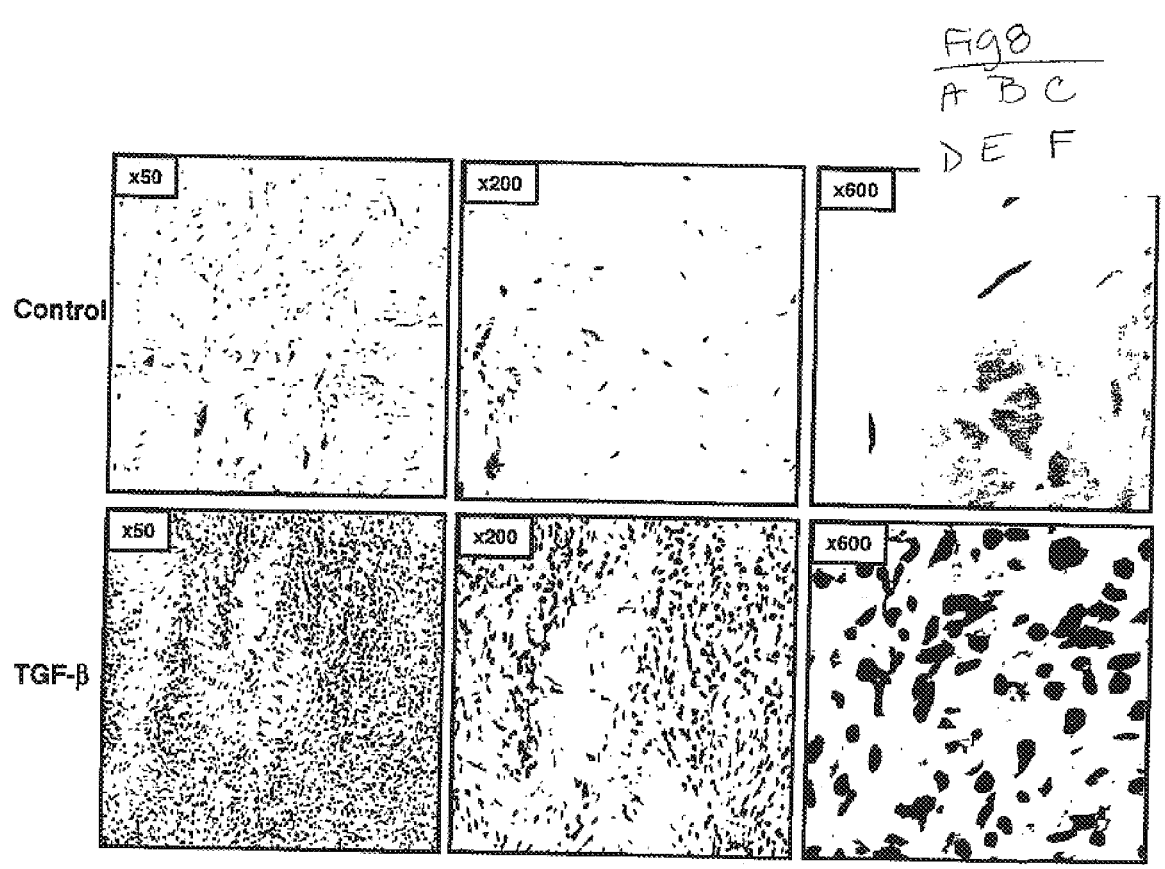

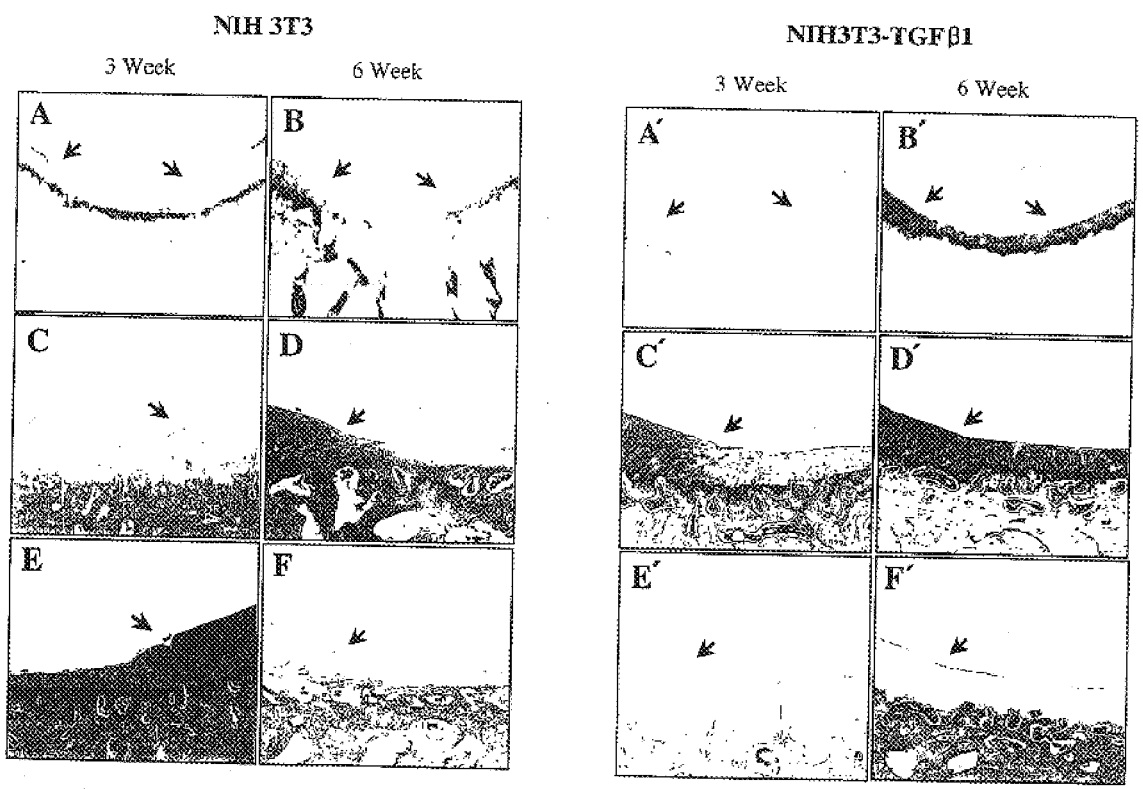
Figure 10. Regeneration of Cartilage with Irradiated NIH3T3-TGF-β1 fibroblast cells Figure 11. Regeneration of Cartilage with Human Foreskin Fibroblast Cells Producing TGF-β1
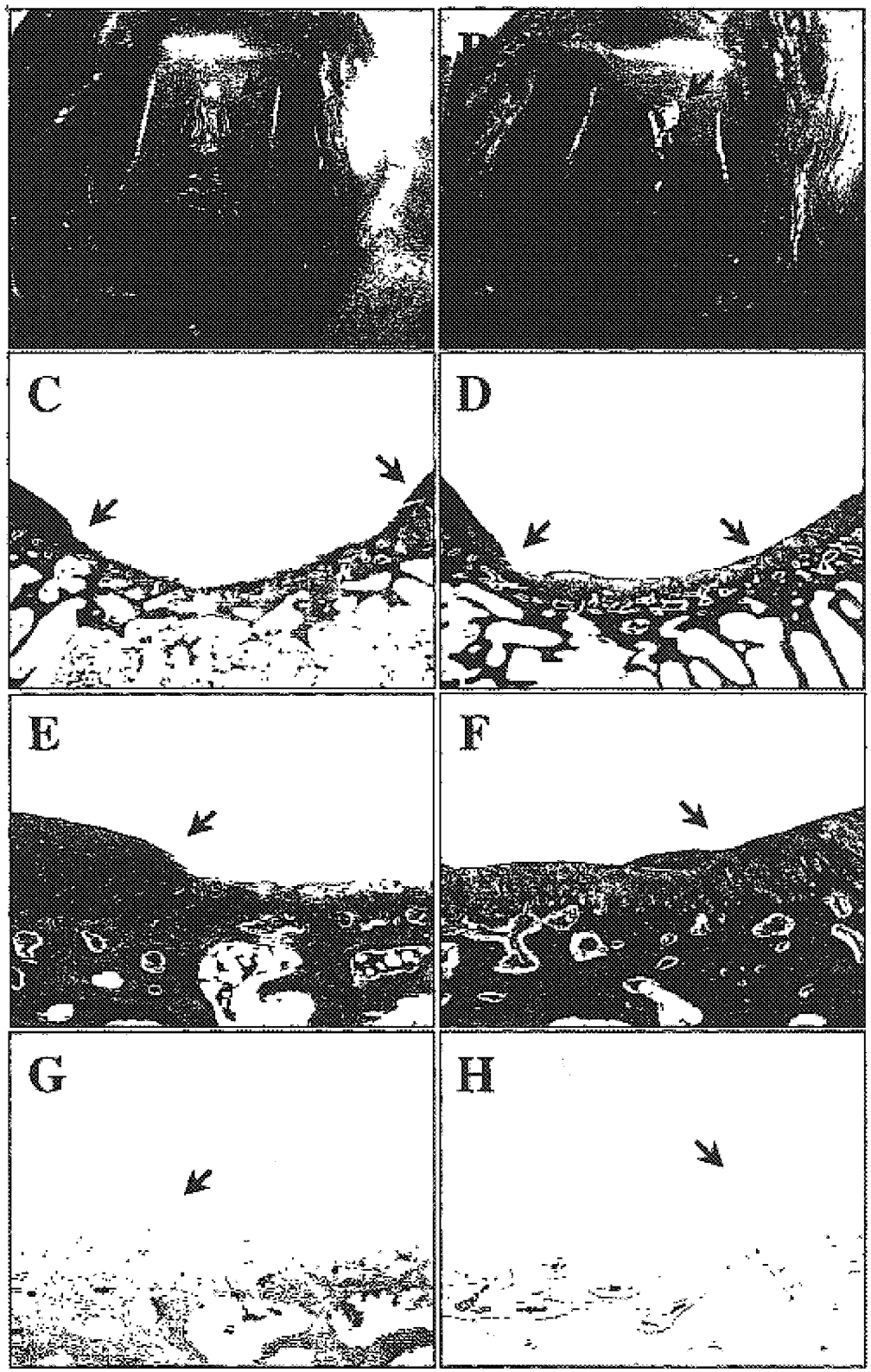

Figure 12. Regeneration of Cartilage with NIH3T3-TGF-β1 cells in a Dog Model
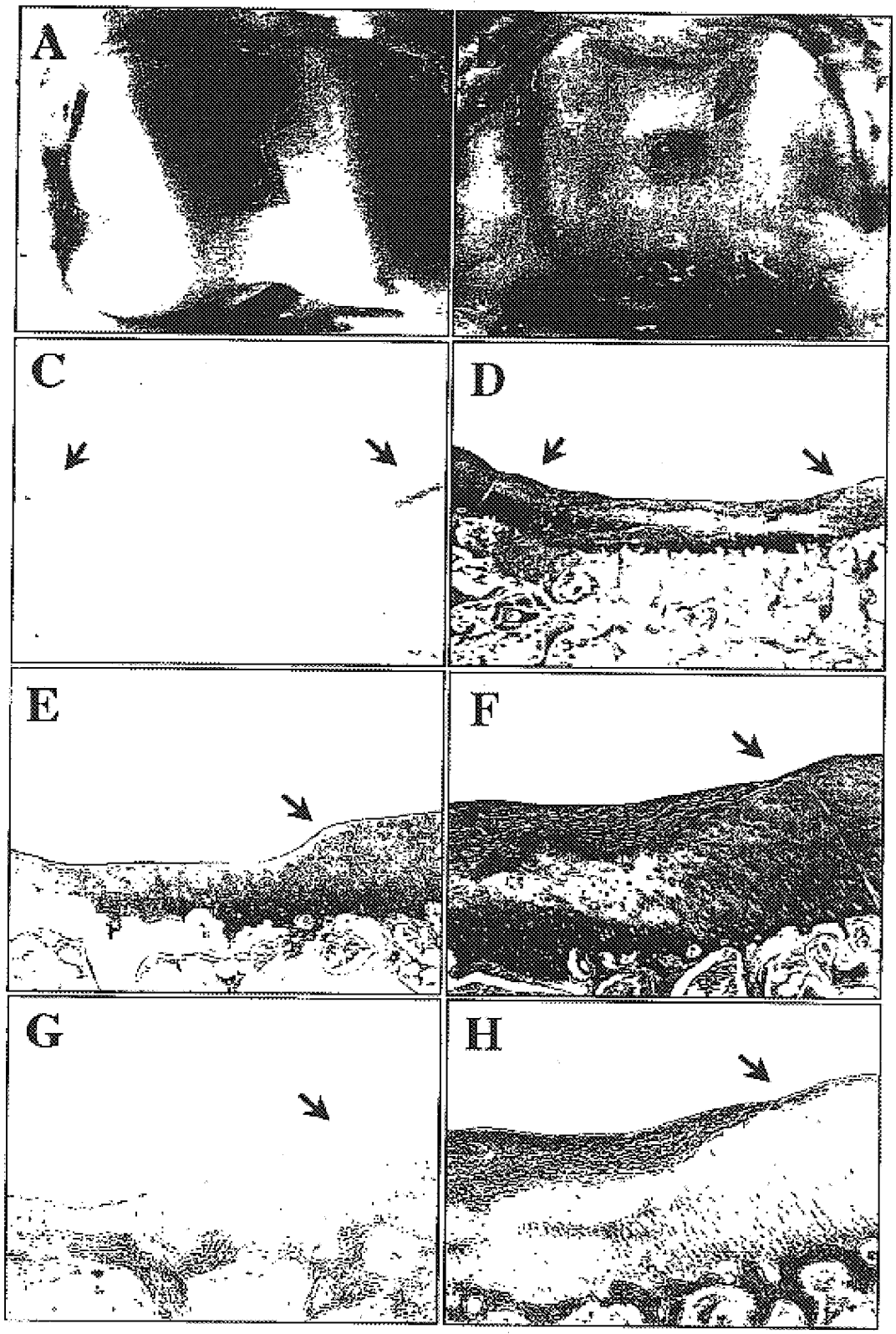

GENE THERAPY USING TGF-β

CONTINUING DATA

The present application is a continuation-in-part application U.S. patent application Ser. No. 09/345,415, filed on Jun. 30, 1999, U.S. Pat. No. 6,315,992, which is incorporated by reference herein in its entirety.

BACKGROUND OF THE INVENTION

1. Field of the Invention

The present invention relates to a method of introducing at least one gene encoding a member of the transforming growth factor β superfamily into at least one mammalian connective tissue for use in regenerating connective tissue in the mammalian host. The present invention also relates to a connective tissue cell line that harbors a DNA vector molecule containing a gene encoding a member of the transforming growth factor β superfamily.

2. Brief Description of the Related Art

In the orthopedic field, degenerative arthritis or osteoarthritis is the most frequently encountered disease associated with cartilage damage. Almost every joint in the body, such as the knee, the hip, the shoulder, and even the wrist, is affected. The pathogenesis of this disease is the degeneration of hyaline articular cartilage (Mankin et al., J Bone Joint Surg, 52A: 460–466, 1982). The hyaline cartilage of the joint becomes deformed, fibrillated, and eventually excavated. If the degenerated cartilage could somehow be regenerated, most patients would be able to enjoy their lives without debilitating pain. There has been no method reported to date to regenerate damaged hyaline cartilage.

Traditional routes of drug delivery, such as oral, intravenous or intramuscular administration, to carry the drug to the joint are inefficient. The half-life of drugs injected intra-articularly is generally short. Another disadvantage of intra-articular injection of drugs is that frequent repeated injections are necessary to obtain acceptable drug levels at the joint spaces for treating a chronic condition such as arthritis. Because therapeutic agents heretofore could not be selectively targeted to joints, it was necessary to expose the mammalian host to systemically high concentrations of drugs in order to achieve a sustained, intra-articular therapeutic dose. Exposure of non-target organs in this manner exacerbated the tendency of anti-arthritis drugs to produce serious side effects, such as gastrointestinal upset and changes in the hematological, cardiovascular, hepatic and renal systems of the mammalian host.

In the orthopedic field, some cytokines have been considered as candidates for the treatment of orthopedic diseases. Bone morphogenic protein has been considered to be an effective stimulator of bone formation (Ozkaynak et al., EMBO J, 9:2085–2093, 1990; Sampath and Rueger, Complications in Ortho, 101–107, 1994), and TGF-β has been reported as a stimulator of osteogenesis and chondrogenesis (Joyce et al., J Cell Biology, 110:2195–2207, 1990).

Transforming growth factor-β (TGF-β is considered to be a multifunctional cytokine (Sporn and Roberts, Nature (London), 332: 217–219, 1988), and plays a regulatory role in cellular growth, differentiation and extracellular matrix protein synthesis (Madri et al., J Cell Biology, 106: 1375–1384, 1988). TGF-β inhibits the growth of epithelial cells and osteoclast-like cells in vitro (Chenu et al., Proc Natl Acad Sci, 85: 5683–5687, 1988), but it stimulates enchondral ossification and eventually bone formation in vivo (Critchlow et al., Bone, 521–527, 1995; Lind et al., A Orthop Scand, 64(5): 553–556, 1993; and Matsumoto et al., In vivo, 8: 215–220, 1994). TGF-β-induced bone formation is mediated by its stimulation of the subperiosteal pluripotential cells, which eventually differentiate into cartilage-forming cells (Joyce et al., J Cell Biology, 110: 2195–2207, 1990; and Miettinen et al., J Cell Biology, 127-6: 2021–2036, 1994).

The biological effect of TGF-β in orthopedics has been reported (Andrew et al., Calcif Tissue In. 52: 74–78, 1993; Borque et al., Int J Dev Biol., 37:573–579, 1993; Carrington et al., J Cell Biology, 107:1969–1975, 1988; Lind et al., A Orthop Scand. 64(5):553–556, 1993; Matsumoto et al., In vivo, 8:215–220, 1994). In mouse embryos, staining shows that TGF-β is closely associated with tissues derived from the mesenchyme, such as connective tissue, cartilage and bone. In addition to embryologic findings, TGF-β is present at the site of bone formation and cartilage formation. It can also enhance fracture healing in rabbit tibiae. Recently, the therapeutic value of TGF-β has been reported (Critchlow et al., Bone, 521–527, 1995; and Lind et al., A Orthop Scand, 64(5): 553–556, 1993), but its short-term effects and high cost have limited wide clinical application.

Intraarticular injection of TGF-β for the treatment of arthritis is not desirable, because the injected TGF-β has a short duration of action, as TGF-β is degraded into inactive form in vivo. Therefore, a new method for long-term release of TGF-β is necessary for the regeneration of hyaline cartilage.

There have been reports of regeneration of articular cartilage with autotransplantation of cartilage cells (Brittberg et al., New Engl J Med 331: 889–895, 1994), but this procedure entails two operations with wide excision of soft tissues. If intraaticular injection is enough for the treatment of degenerative arthritis, it will be of great economic and physical benefit to the patients.

Gene therapy, which is a method of transferring a specific protein to a specific site, may be the answer to this problem (Wolff and Lederberg, Gene Therapeutics ed. Jon A. Wolff, Mar. 25, 1994; and Jenks, J Natl Cancer Inst, 89(16): 1182–1184, 1997).

U.S. Pat. Nos. 5,858,355 and 5,766,585 disclose making a viral or plasmid construct of the IRAP (interleukin-1 receptor antagonist protein) gene; transfecting synovial cells U.S. Pat. No. (5,858,355) and bone marrow cells U.S. Pat. No. (5,766,585) with the construct; and injecting the transfected cells into a rabbit joint, but there is no disclosure of using a gene belonging to the TGF-β superfamily to regenerate connective tissue.

U.S. Pat. Nos. 5,846,931 and 5,700,774 disclose injecting a composition that includes a bone morphogenesis protein (BMP), which belongs to the TGF β "superfamily", together with a truncated parathyroid hormone related peptide to effect the maintenance of cartilaginous tissue formation, and induction of cartilaginous tissue. However, there is no disclosure of a gene therapy method using the BMP gene.

In spite of these prior art disclosures, there remains a very real and substantial need for a method of introducing at least one gene encoding a product into at least one cell of a connective tissue of a mammalian host in vitro, or alternatively in vivo, for use in treating the mammalian host. Further, there is a need for a process wherein a gene encoding a member of the transforming growth factor β superfamily is used to regenerate connective tissue in the mammalian host. More specifically, there is a need for a process where a gene coding for a TGF-β superfamily of proteins is expressed in host connective tissue cells in vivo.

SUMMARY OF THE INVENTION

The present invention has met the hereinbefore described need. A method of introducing at least one gene encoding a product into at least one cell of a mammalian connective tissue for use in treating a mammalian host is provided in the present invention. This method includes employing recombinant techniques to produce a DNA vector molecule containing the gene coding for the product and introducing the DNA vector molecule containing the gene coding for the product into the connective tissue cell. The DNA vector molecule can be any DNA molecule capable of being delivered and maintained within the target cell or tissue such that the gene encoding the product of interest can be stably expressed. The DNA vector molecule preferably utilized in the present invention is either a viral or plasmid DNA vector molecule. This method preferably includes introducing the gene encoding the product into the cell of the mammalian connective tissue for a therapeutic use.

The present invention is directed to a method of treating arthritis comprising:
 a) generating a recombinant viral or plasmid vector comprising a DNA sequence encoding a member of a transforming growth factor superfamily of proteins operatively linked to a promoter;
 b) transfecting in vitro a population of cultured connective tissue cells with said recombinant vector, resulting in a population of transfected connective tissue cells; and
 c) transplanting the transfected connective tissue cells by intraarticular injection to an arthritic joint space of a mammalian host, such that expression of the DNA sequence within the joint space results in regenerating connective tissue.

The recombinant vector may be, but not limited to, a retroviral vector, preferably a retroviral vector. The vector may also be a plasmid vector.

The method of the invention includes storing a population of transfected connective tissue cells prior to transplantation. The cells may be stored in 10% DMSO under liquid nitrogen prior to transplantation.

The connective tissue cells include, but are not limited to, fibroblast cells, mesenchymal cells, osteoblasts, or chondrocytes. The fibroblast cells may be NIH 3T3 cells or human foreskin fibroblast cells.

The connective tissue includes, but is not limited to, cartilage, ligament, or tendon. The cartilage may be hyaline cartilage.

The method of the present invention uses a member of the transformation growth factor superfamily, which includes transforming growth factor β (TGF-β). The member of the transformation growth factor superfamily may be TGF-β1, TGF-β2, TGF-β3, BMP-2, BMP-3, BMP-4, BMP-5, BMP-6, or BMP-7. Preferably, TGF-β is human or porcine TGF-β1, TGF-β2 or TGF-β3.

The present invention is also directed to a method of regenerating hyaline cartilage, comprising:
 a) generating a recombinant viral or plasmid vector comprising a DNA sequence encoding a member of a transforming growth factor superfamily of proteins operatively linked to a promoter;
 b) transfecting in vitro a population of cultured connective tissue cells with the recombinant vector, resulting in a population of transfected connective tissue cells; and
 c) transplanting the transfected connective tissue cells by intraarticular injection to joint space of a mammalian host, such that expression of the DNA sequence within the joint space results in regenerating hyaline cartilage.

The transfection method may be accomplished by methods such as liposome encapsulation, calcium phosphate coprecipitation, electroporation and DEAE-dextran mediation.

The method of the invention includes using preferably the plasmid pmTβ1.

The present invention is also directed to a connective tissue cell line comprising a recombinant viral or plasmid vector comprising a DNA sequence encoding a member of the transforming growth factor superfamily. The connective tissue cell line may include, but is not limited to, a fibroblast cell line, a mesenchymal cell line, a chondrocyte cell line, an osteoblast cell line, or an osteocyte cell line. The fibroblast cell line may be a human foreskin fibroblast cell line or NIH 3T3 cell line.

The connective tissue cell line according to the invention comprises a member of the transforming growth factor superfamily. Preferably, a member of the transforming growth factor superfamily is TGF-β1, TGF-β2, TGF-β3, BMP-2, BMP-3, BMP-4, BMP-5, BMP-6, or BMP-7. More preferably, the member is human or porcine TGF-β1, TGF-β2 or TGF-β3.

The connective tissue cell line of the invention also may comprise cells harboring the recombinant vector pmTβ1.

These and other objects of the invention will be more fully understood from the following description of the invention, the referenced drawings attached hereto and the claims appended hereto.

5A. In the partially damaged area, the regenerated hyaline cartilage is shown by H&E staining (black arrow).

5B. In the completely denuded cartilage area, the regenerated tissue (white arrow) was fibrous collagen.

Figure 6:
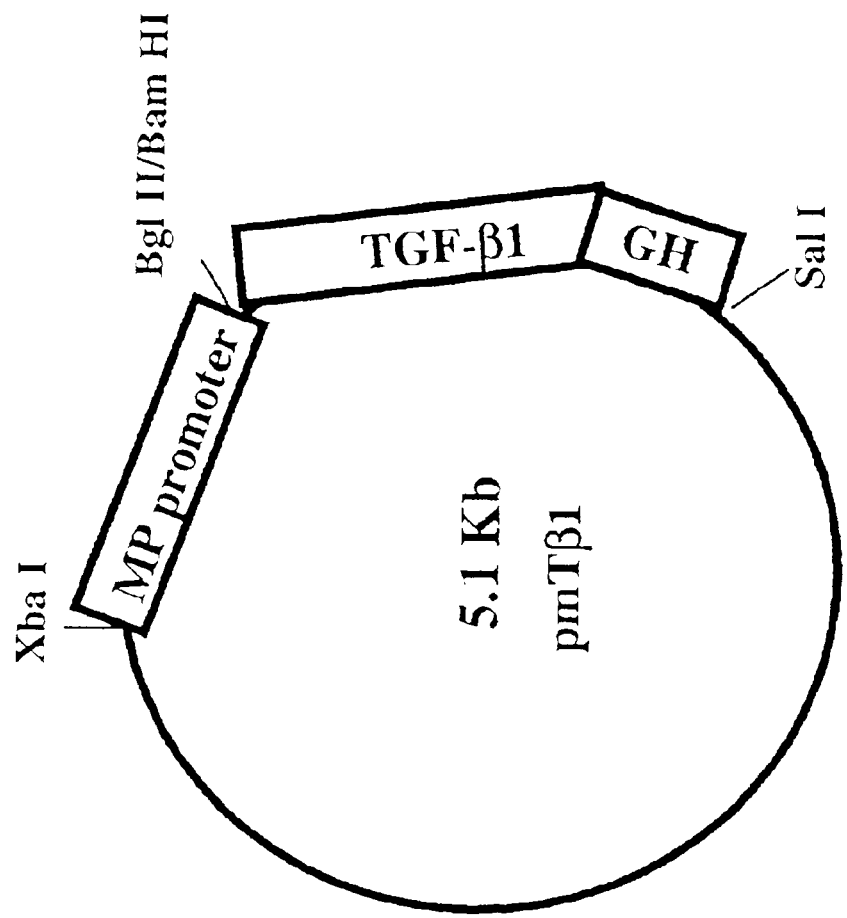

FIG. 6—Plasmid map of pmTβ1.

FIGS. 7A–7D—Gross morphology of rabbit achilles tendon injected with TGF-β1 transfected cells.

7A. Tendon injected with control cells.

7B. Tendon injected with TGF-β1 transfected cells, six weeks after injection.

7C. Cross-sectional view of the tendon pictured in 7A.

7D. Cross-sectional view of the tendon pictured in 7B.

FIGS. 8A–8F—Microscopic findings of regenerated tissue in rabbit achilles tendon with H&E staining.

8A, 8B and 8C show tendon injected with control cells 6 weeks after injection. 8A. ×50 magnification. 8B. ×200 magnification. 8C. ×600 magnification.

8D, 8E and 8F show tendon injected with TGF-β1 transfected cells 6 weeks after injection. 8D. ×50 magnification. 8E. ×200 magnification. 8F. ×600 magnification. The TGF-β1 transfected cells injected into the tendon appear to be more round than the endogenous tendon cells. Fibrous collagen was produced by autocrine and paracrine modes of action, and the tendon was enlarged. The tendon was enlarged after the injection of TGF-β1 transfected cells.

FIGS. 9A–9B—Microscopic findings of regenerated tissue in rabbit achilles tendon with H&E staining (A) and Immunohistochemical staining (B) with TGF-β1 antibody. Brown immunoperoxidase reaction product indicates high levels of recombinant TGF-β1 expression in the NIH 3T3-TGF-β1 cells.

FIGS. 10A–F and A'–F'—Regeneration of cartilage with irradiated NIH3T3-TGF-β1 fibroblast cells.

FIGS. 11A–H—Regeneration of cartilage with human foreskin fibroblast cells producing TGF-β1.

FIGS. 12A–H—Regeneration of cartilage with NIH3T3-TGF-β1 cells in a dog model.

DETAILED DESCRIPTION OF THE INVENTION

As used herein, the term "patient" includes members of the animal kingdom including but not limited to human beings.

As used herein, the term "mammalian host" includes members of the animal kingdom including but not limited to human beings.

As used herein, the term "connective tissue" is any tissue that connects and supports other tissues or organs, and includes but is not limited to a ligament, a cartilage, a tendon, a bone, and a synovium of a mammalian host.

As used herein, the term "connective tissue cell" or "cell of a connective tissue" include cells that are found in the connective tissue, such as fibroblasts, cartilage cells (chondrocytes), and bone cells (osteoblasts/osteocytes), which secrete collagenous extracellular matrix, as well as fat cells (adipocytes) and smooth muscle cells. Preferably, the connective tissue cells are fibroblasts, cartilage cells, and bone cells. More preferably, the connective tissue cells are fibroblast cells. Connective tissue cells also include mesenchymal cells which are also known as immature fibroblasts. It will be recognized that the invention can be practiced with a mixed culture of connective tissue cells, as well as cells of a single type. It is also recognized that the tissue cells may be treated such as by chemical or radiation so that the cells stably express the gene of interest, preferably TGF-β.

As used herein, "connective tissue cell line" includes a plurality of connective tissue cells originating from a common parent cell.

As used herein, "hyaline cartilage" refers to the connective tissue covering the joint surface. By way of example only, hyaline cartilage includes, but is not limited to, articular cartilage, costal cartilage, and nose cartilage.

In particular, hyaline cartilage is known to be self-renewing, responds to alterations, and provides stable movement with less friction. Hyaline cartilage found even within the same joint or among joints varies in thickness, cell density, matrix composition and mechanical properties, yet retains the same general structure and function. Some of the functions of hyaline cartilage include surprising stiffness to compression, resilience, and exceptional ability to distribute weight loads, ability to minimize peak stress on subchondral bone, and great durability.

Grossly and histologically, hyaline cartilage appears as a slick, firm surface that resists deformation. The extracellular matrix of the cartilage comprises chondrocytes, but lacks blood vessels, lymphatic vessels or nerves. An elaborate, highly ordered structure that maintains interaction between chondrocytes and the matrix serves to maintain the structure and function of the hyaline cartilage, while maintaining a low level of metabolic activity. The reference O'Driscoll, J. Bone Joint Surg., 80A: 1795–1812, 1998 describes the structure and function of hyaline cartilage in detail, which is incorporated herein by reference in its entirety.

As used herein, the "transforming growth factor-β (TGF-β) superfamily" encompasses a group of structurally-related proteins which affect a wide range of differentiation processes during embryonic development. The family includes, Müllerian inhibiting substance (MIS), which is required for normal male sex development (Behringer, et al., Nature, 345:167, 1990), Drosophila decapentaplegic (DPP) gene product, which is required for dorsal-ventral axis formation and morphogenesis of the imaginal disks (Padgett, et al., Nature, 325:81–84, 1987), the Xenopus Vg-1 gene product, which localizes to the vegetal pole of eggs (Weeks, et al., Cell, 51:861–867, 1987), the activins (Mason, et al., Biochem, Biophys. Res. Commun., 135:957–964, 1986), which can induce the formation of mesoderm and anterior structures in Xenopus embryos (Thomsen, et al., Cell, 63:485, 1990), and the bone morphogenetic proteins (BMP's, such as BMP-2, 3, 4, 5, 6 and 7, osteogenin, OP-1) which can induce de novo cartilage and bone formation (Sampath, et al., J. Biol. Chem., 265:13198, 1990). The TGF-β gene products can influence a variety of differentiation processes, including adipogenesis, myogenesis, chondrogenesis, hematopoiesis, and epithelial cell differentiation (for a review, see Massague, Cell 49:437, 1987), which is incorporated herein by reference in its entirety.

The proteins of the TGF-β family are initially synthesized as a large precursor protein which subsequently undergoes proteolytic cleavage at a cluster of basic residues approximately 110–140 amino acids from the C-terminus. The C-terminal regions of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. For most of the family members that have been studied, the homodimeric species has been found to be biologically active, but for other family members, like the inhibins (Ung, et al., Nature, 321:779, 1986) and the TGF-β's (Cheifetz, et al., Cell, 48:409, 1987), heterodimers have also been detected, and these appear to have different biological properties than the respective homodimers.

Members of the superfamily of TGF-β genes include TGF-β3, TGF-β2, TGF-β4 (chicken), TGF-β1, TGF-β5 (Xenopus), BMP-2, BMP-4, Drosophila DPP, BMP-5, BMP-6, Vgr1, OP-1/BMP-7, Drosophila 60A, GDF-1, Xenopus Vgf, BMP-3, Inhibin-βA, Inhibin-βB, Inhibin-α, and MIS. These genes are discussed in Massague, Ann. Rev. Biochem. 67:753–791, 1998, which is incorporated herein by reference in its entirety.

Preferably, the member of the superfamily of TGF-β genes is TGF-β. More preferably, the member is TGF-β1, TGF-β2, TGF-β3, BMP-2, BMP-3, BMP-4, BMP-5, BMP-6, or BMP-7. Even more preferably, the member is human or porcine TGF-β. Still more preferably, the member is human or porcine TGF-β1, TGF-β2, or TGF-β3. Most preferably, the member is human or porcine TGF-β1.

As used herein, "selectable marker" includes a gene product that is expressed by a cell that stably maintains the introduced DNA, and causes the cell to express an altered phenotype such as morphological transformation, or an enzymatic activity. Isolation of cells that express a transfected gene is achieved by introduction into the same cells a second gene that encodes a selectable marker, such as one having an enzymatic activity that confers resistance to an antibiotic or other drug. Examples of selectable markers include, but are not limited to, thymidine kinase, dihydrofolate reductase, aminoglycoside phosphotransferase, which confers resistance to aminoglycoside antibiotics such as kanamycin, neomycin and geneticin, hygromycin B phosphotransferase, xanthine-guanine phosphoribosyl transferase, CAD (a single protein that possesses the first three enzymatic activities of de novo uridine biosynthesis— carbamyl phosphate synthetase, aspartate transcarbamylase and dihydroorotase), adenosine deaminase, and asparagine synthetase (Sambrook et al. Molecular Cloning, Chapter 16. 1989), incorporated herein by reference in its entirety.

As used herein, a "promoter" can be any sequence of DNA that is active, and controls transcription in an eucaryotic cell. The promoter may be active in either or both eucaryotic and procaryotic cells. Preferably, the promoter is active in mammalian cells. The promoter may be constitutively expressed or inducible. Preferably, the promoter is inducible. Preferably, the promoter is inducible by an external stimulus. More preferably, the promoter is inducible by hormones or metals. Still more preferably, the promoter is inducible by heavy metals. Most preferably, the promoter is a metallothionein gene promoter. Likewise, "enhancer elements", which also control transcription, can be inserted into the DNA vector construct, and used with the construct of the present invention to enhance the expression of the gene of interest.

As used herein, the term "DC-chol" means a cationic liposome containing cationic cholesterol derivatives. The "DC-chol" molecule includes a tertiary amino group, a medium length spacer arm (two atoms) and a carbamoyl linker bond (Gao et al., Biochem. Biophys. Res, Commun., 179:280–285, 1991).

As used herein, "SF-chol" is defined as a type of cationic liposome.

As used herein, the term "biologically active" used in relation to liposomes denotes the ability to introduce functional DNA and/or proteins into the target cell.

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As used herein, the term "maintenance", when used in the context of liposome delivery, denotes the ability of the introduced DNA to remain present in the cell. When used in other contexts, it means the ability of targeted DNA to remain present in the targeted cell or tissue so as to impart a therapeutic effect.

The present invention discloses ex vivo and in vivo techniques for delivery of a DNA sequence of interest to the connective tissue cells of the mammalian host. The ex vivo technique involves culture of target connective tissue cells, in vitro transfection of the DNA sequence, DNA vector or other delivery vehicle of interest into the connective tissue cells, followed by transplantation of the modified connective tissue cells to the target joint of the mammalian host, so as to effect in vivo expression of the gene product of interest.

As an alternative to the in vitro manipulation of fibroblast cells, the gene encoding the product of interest is introduced into liposomes and injected directly into the area of the joint, where the liposomes fuse with the connective tissue cells, resulting in an in vivo gene expression of the gene product belonging to the TGF-β superfamily.

As an additional alternative to the in vitro manipulation of connective tissue cells, the gene encoding the product of interest is introduced into the area of the joint as naked DNA. The naked DNA enters the connective tissue cell, resulting in an in vivo gene expression of the gene product belonging to the TGF-β superfamily.

One ex vivo method of treating a connective tissue disorder disclosed throughout this specification comprises initially generating a recombinant viral or plasmid vector which contains a DNA sequence encoding a protein or biologically active fragment thereof. This recombinant vector is then used to infect or transfect a population of in vitro cultured connective tissue cells, resulting in a population of connective cells containing the vector. These connective tissue cells are then transplanted to a target joint space of a mammalian host, effecting subsequent expression of the protein or protein fragment within the joint space. Expression of this DNA sequence of interest is useful in substantially reducing at least one deleterious joint pathology associated with a connective tissue disorder.

It will be understood by the artisan of ordinary skill that the preferred source of cells for treating a human patient is the patient's own connective tissue cells, such as autologous fibroblast cells.

More specifically, this method includes employing as the gene a gene capable of encoding a member of the transforming growth factor β superfamily, or a biologically active derivative or fragment thereof and a selectable marker, or a biologically active derivative or fragment thereof.

A further embodiment of the present invention includes employing as the gene a gene capable of encoding at least one of a member of transforming growth factor β superfamily or a biologically active derivative or fragment thereof, and employing as the DNA plasmid vector any DNA plasmid vector known to one of ordinary skill in the art capable of stable maintenance within the targeted cell or tissue upon delivery, regardless of the method of delivery utilized.

One such method is the direct delivery of the DNA vector molecule, whether it be a viral or plasmid DNA vector molecule, to the target cell or tissue. This method also includes employing as the gene a gene capable of encoding a member of transforming growth factor β superfamily or biologically active derivative or fragment thereof.

Another embodiment of this invention provides a method for introducing at least one gene encoding a product into at least one cell of a connective tissue for use in treating the mammalian host. This method includes employing non-viral means for introducing the gene coding for the product into the connective tissue cell. More specifically, this method includes a liposome encapsulation, calcium phosphate coprecipitation, electroporation, or DEAE-dextran mediation, and includes employing as the gene a gene capable of encoding a member of transforming growth factor superfamily or biologically active derivative or fragment thereof, and a selectable marker, or biologically active derivative or fragment thereof.

Another embodiment of this invention provides an additional method for introducing at least one gene encoding a product into at least one cell of a connective tissue for use in treating the mammalian host. This additional method includes employing the biologic means of utilizing a virus to deliver the DNA vector molecule to the target cell or tissue. Preferably, the virus is a pseudo-virus, the genome having been altered such that the pseudovirus is capable only of delivery and stable maintenance within the target cell, but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue.

A preferred embodiment of the invention is a method of delivering TGF-β to a target joint space by delivering the TGF-β gene to the connective tissue of a mammalian host through use of a retroviral vector with the ex vivo technique disclosed within this specification. In other words, a DNA sequence of interest encoding a functional TGF-β protein or protein fragment is subcloned into a retroviral vector of choice, the recombinant viral vector is then grown to adequate titer and used to infect in vitro cultured connective tissue cells, and the transduced connective tissue cells, preferably autografted cells, are transplanted into the joint of interest, preferably by intra-articular injection.

Another preferred method of the present invention involves direct in vivo delivery of a TGF-β superfamily gene to the connective tissue of a mammalian host through use of either an adenovirus vector, adeno-associated virus (AAV) vector or herpes-simplex virus (HSV) vector. In other words, a DNA sequence of interest encoding a functional TGF-β protein or protein fragment is subcloned into the respective viral vector. The TGF-β containing viral vector is then grown to adequate titer and directed into the joint space, preferably by intra-articular injection.

Direct intra-articular injection of a DNA molecule containing the gene of interest into the joint results in transfection of the recipient connective tissue cells and hence bypasses the requirement of removal, in vitro culturing, transfection, selection, as well as transplanting the DNA vector containing-fibroblast to promote stable expression of the heterologous gene of interest.

Methods of presenting the DNA molecule to the target connective tissue of the joint includes, but is not limited to, encapsulation of the DNA molecule into cationic liposomes, subcloning the DNA sequence of interest in a retroviral or plasmid vector, or the direct injection of the DNA molecule itself into the joint. The DNA molecule, regardless of the form of presentation to the knee joint, is preferably presented as a DNA vector molecule, either as recombinant viral DNA vector molecule or a recombinant DNA plasmid vector molecule. Expression of the heterologous gene of interest is ensured by inserting a promoter fragment active in eukaryotic cells directly upstream of the coding region of the heterologous gene. One of ordinary skill in the art may utilize known strategies and techniques of vector construction to ensure appropriate levels of expression subsequent to entry of the DNA molecule into the connective tissue.

In a preferred embodiment, fibroblasts recovered from the knee joint are cultured in vitro for subsequent utilization as a delivery system for gene therapy. It will be apparent that Applicants are not limited to the use of the specific connective tissue disclosed. It would be possible to utilize other tissue sources for in vitro culture techniques. The method of using the gene of this invention may be employed both prophylactically and in the therapeutic treatment of arthritis. It will also be apparent that Applicants are not limited to prophylactic or therapeutic applications in treating only the knee joint. It would be possible to utilize the present invention either prophylactically or therapeutically to treat arthritis in any susceptible joint.

In another embodiment of this invention, a compound for parenteral administration to a patient in a therapeutically effective amount is provided that contains a gene encoding a TGF-β superfamily protein and a suitable pharmaceutical carrier.

Another embodiment of this invention provides for a compound for parenteral administration to a patient in a prophylactically effective amount that includes a gene encoding a TGF-β superfamily protein and a suitable pharmaceutical carrier.

A further embodiment of this invention includes the method as hereinbefore described including introducing the gene into the cell in vitro. This method also includes subsequently transplanting the infected cell into the mammalian host. This method includes after effecting the transfecting of the connective tissue cell but before the transplanting of the infected cell into the mammalian host, storing the transfected connective tissue cell. It will be appreciated by those skilled in the art that the infected connective tissue cell may be stored frozen in 10 percent DMSO in liquid nitrogen. This method includes employing a method to substantially prevent the development of arthritis in a mammalian host having a high susceptibility of developing arthritis.

Another embodiment of this invention includes a method of introducing at least one gene encoding a product into at least one cell of a connective tissue of a mammalian host for use in treating the mammalian host as hereinbefore described including effecting in vivo the infection of the cell by introducing the viral vector containing the gene coding for the product directly into the mammalian host. Preferably, this method includes effecting the direct introduction into the mammalian host by intra-articular injection. This method includes employing the method to substantially prevent a development of arthritis in a mammalian host having a high susceptibility of developing arthritis. This method also includes employing the method on an arthritic mammalian host for therapeutic use. Further this method also includes employing the method to repair and regenerate the connective tissue as hereinbefore defined.

It will be appreciated by those skilled in the art, that the viral vectors employing a liposome are not limited by cell division as is required for the retroviruses to effect infection and integration of connective tissue cells. This method employing non-viral means as hereinbefore described includes employing as the gene a gene capable of encoding a member belonging to the TGF-β superfamily and a selectable marker gene, such as an antibiotic resistance gene.

Another embodiment of the present invention is delivery of a DNA sequence encoding a member of the TGF-β superfamily to the connective tissue of a mammalian host by any of the methods disclosed within this specification so as to effect in vivo expression of collagen to regenerate connective tissue, such as cartilage.

In a specific method disclosed as an example, and not as a limitation to the present invention, a DNA plasmid vector containing the TGF-β coding sequence was ligated downstream of the metallothionein promoter.

Connective tissues are difficult organs to target therapeutically. Intravenous and oral routes of drug delivery that are known in the art provide poor access to these connective tissues and have the disadvantage of exposing the mammalian host body systemically to the therapeutic agent. More specifically, known intra-articular injection of proteins to joints provides direct access to a joint. However, most of the injected drugs in the form of encapsulated proteins have a short intra-articular half-life. The present invention solves these problems by introducing into the connective tissue of a mammalian host genes coding for proteins that may be used to treat the mammalian host. More specifically, this invention provides a method for introducing into the connective tissue of a mammalian host genes coding for proteins with anti-arthritic properties.

In the invention, gene therapy was applied to solve the problem of short duration of action and high cost associated with administering TGF-β. The transfected cells could survive for more than 6 weeks in tissue cultures without morphological change. To determine the viability and duration of action, the cells were injected into rabbit achilles tendon. If the nutritional supply is adequate for the cells in vivo, the cells could survive and produce TGF-β for a long enough period of time to stimulate the surrounding cells. The cells were functional in both the intratendinous and intraarticular environment.

The concentration of transfected cells is an important factor for local action. In a previous experiment (Joyce et al., supra, 1990), the dose of TGF-β determined the type of tissue formed. In particular, the ratio of cartilage formation to intramembranous bone formation decreased as the dose was lowered. TGF-β is also biphasic in stimulation of primary osteoblasts and MC3T3 cells (Centrella et al., Endocrinology, 119:2306–2312, 1986). That is, it can be both stimulatory and inhibitory according to the concentration (Chenu et al., Proc Natl Acad Sci, 85:5683–5687, 1988). In the Examples provided herein, the NIH 3T3-TGF-β1 cells stimulated collagen synthesis in different concentrations of $10^4$, $10^5$, and $10^6$ cells/ml. The tendon was enlarged mostly with the concentration of $10^6$ cells/ml.

In the Examples, the joint was injected with 0.3 ml of $10^6$ cells/ml concentration. The specimens were harvested from 2 weeks to 6 weeks after injection. The environment in the joint is different from that of the tendon. The cells can move freely within the joint. They will move to the area with specific affinity for the cells. The synovium, meniscus and cartilage defect areas are the possible sites for cellular adhesion. At six weeks after injection, the regenerated tissues were observed at the partially and completely damaged cartilage defect areas, but not at the synovium or the meniscus. This specific affinity for the damaged area is another advantage for clinical application. If degenerative arthritis can be cured with just injection of cells into the joint, the patients can be treated conveniently without major surgery.

The TGF-β secreted by injected cells can stimulate hyaline cartilage regeneration by two possible ways. One is that the cartilage cells remaining in the damaged area produce the TGF-β receptors at their cell surface (Brand et al., J Biol Chem, 270:8274–8284, 1995; Cheifetz et al., Cell, 48:409–415, 1987; Dumont et al., M Cell Endo, 111:57–66, 1995; Lopez-Casillas et al., Cell, 67:785–795, 1991; Miettinen et al., J Cell Biology, 127:6, 2021–2036, 1994; and Wrana et al., Nature, 370:341–347, 1994). These receptors may have been stimulated by TGF-β secreted by injected cells, which adhere to the damaged area. Because TGF-β is secreted in a latent form in vivo (Wakefield et al., J Biol Chem, 263, 7646–7654, 1988), the latent TGF-β needs an activation process. The other way is that the latent TGF-β or the TGF-β secreted from the transfected cells may have bound to the TGF-β binding protein (LTBT) at the extracellular matrix of partially damaged cartilage layers (Dallas et al., J Cell Biol, 131:539–549, 1995).

Whatever the mechanism of action is, the finding of hyaline cartilage synthesis indicates that a long duration of high TGF-β concentration can stimulate hyaline cartilage regeneration. The vehicle for local high concentration may not be the critical factor for local stimulation, but theoretically, the cartilage cell may be the most suitable vehicle for delivering TGF-β to damaged areas of the cartilage (Brittberg et al., New Engl J Med 331:889–895, 1994). The collagen bilayer matrix is another possible vehicle for local distribution of transfected cells (Frenkel et al., J Bone J Surg (Br) 79-B:831–836, 1997).

Figure 4:
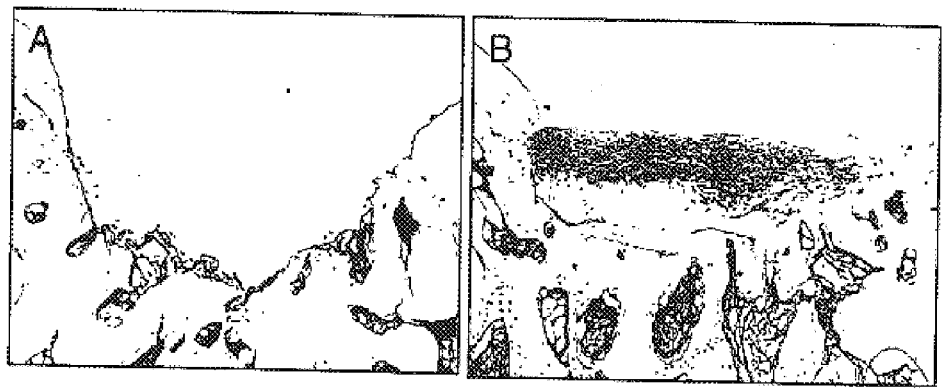
FIGS. 4A–4B—Immunohistochemical analysis for TGF-β1 expression in rabbit joint x 200.
 Brown immunoperoxidase reaction product indicates high levels of recombinant TGF-β1 expression in the NIH3T3-TGF-β1 cells (4B).
 4A show hyaline cartilage in a rabbit joint injected with control cells.
Figure 5:
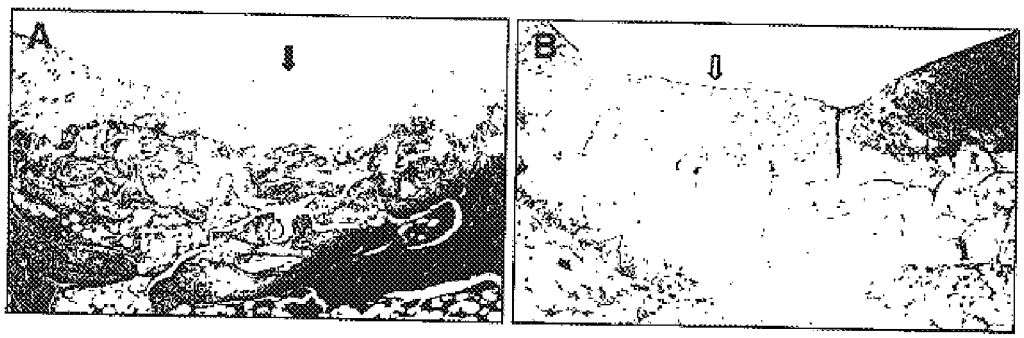
FIGS. 5A–5B—Microscopic findings (×200) of regenerated tissues with H&E staining (A) and Safranin-O staining (B).

The properties of newly formed tissue were determined by a histological method. In H&E staining, the newly formed tissue was identical to surrounding hyaline cartilage (FIG. 4). To evaluate the properties of newly formed tissue, the tissues were stained with Safranin-O (Rosenburg, J Bone Joint Surg, 53A:69–82, 1971). In contrast to the white color of fibrous collagen, the newly formed tissue stained red, suggesting that it is hyaline cartilage (FIG. 5).

The cells in the completely damaged area produced fibrous collagen. The surrounding osteoblastic cells may not have been stimulated because of the osteoid matrix barrier to TGF-β stimulation. Instead of stimulating surrounding cells, the NIH 3T3-TGF-β1 cells produced the fibrous collagen by autocrine stimulation. The fact that the cells were stimulated by both autocrine and paracrine activation increases the likelihood of treatment of degenerative arthritis with chondrocytes that have been stably transfected with TGF-β1 expression constructs.

The cell lines stably transfected with TGF-β1 expression constructs can survive in tendons and knee joints. The cell lines produce fibrous collagen in the tendon and the completely damaged cartilage area. However, the cell lines produce hyaline cartilage in the partially damaged articular cartilage. The mechanism of stimulation by autocrine and paracrine modes of action indicates that gene therapy with a member of the TGF-β superfamily of genes is a new treatment method for hyaline cartilage injury.

The inventors made stable fibroblast (NIH 3T3-TGF-β1, and human foreskin fibroblast TGF-β1) cell line by transfecting TGF-β1 expression constructs. These TGF-β- producing cells maintained high concentration of active TGF-β concentration in vivo for a long duration.

The first question to be answered regarding the possibility of gene therapy and, in particular, cell-mediated gene therapy is the viability of the cells in vivo. Even though TGF-β can suppress the immune cells in vitro, the cells may not be able to survive in the tissue of other species with highly effective immune surveillance systems. Secondly, the optimum concentration for gene expression in vivo should be evaluated. We injected the cells into rabbit achilles tendon in three different concentrations to answer this question. The concentration of intraarticular injection to be used was determined from the optimal concentration for intratendinous injection. The third question is how the cells stimulate the regeneration of cartilage within the joint.

There are two modes of action for the injected cells. One is the activation of surrounding cells by secreted TGF-β (paracrine activation)(Snyder, Sci Am, 253(4): 132–140, 1985), and the other is self-activation (autocrine activation). The concentration of cells may affect the pathways, but the surrounding environment may be the most important factor for the determination of action mode. Intraarticular joint fluid and the interior of a ligament are two different environments in terms of blood supply, nutritional supply and surrounding cells. The transfected cells were injected into two different environments to find out the mode of action of the cells. The overall purpose of this study was to evaluate TGF-β-mediated gene therapy for orthopedic diseases and to ascertain the mode of action in vivo.

The following examples are offered by way of illustration of the present invention, and not by way of limitation.

EXAMPLES

Example I

Materials and Methods
Plasmid Construction

To generate the metallothionein expression construct (pM), the metallothionein I promoter (−660/+63) was generated by polymerase chain amplification using genomic DNA using Xba I and Bam HI restriction sites built into the oligonucleotides used for amplification. The amplified fragment was subcloned into Xba I-Bam HI sites of pBluescript (Stratagene, La Jolla, Calif.). The plasmid pmTβ1 was generated by subcloning a 1.2-kb Bgl II fragment containing the TGF-β1 coding sequence and a growth hormone poly A site at the 3' end into the Bam HI-Sal I sites of pM.

Cell Culture and Transfections—The TGF-β cDNA was transfected into fibroblasts (NIH 3T3-TGF-β1) or human foreskin fibroblast/TGF-β1. They were cultured in Dulbecco's Modified Eagle's Medium (GIBCO-BRL, Rockville, Md.) with 10% concentration of fetal bovine serum. The TGFβ1 cDNA sequence was added into the pmTβ1 vector with a metallothionein gene promoter. A neomycin resistance gene sequence was also inserted into the vector.

The calcium phosphate method to insert this vector into the cells was used. To select the cells with the transfected gene sequence, neomycin (300 µg/ml) was added into the medium. Then, the surviving colonies were selected and the expression of TGF-β1 mRNA was confirmed by Northern analysis and TGF-β1 ELISA assay (R & D Systems). The cells with TGF-β1 expression were stored in liquid nitrogen and cultured just before the injection.

Northern Blot analysis—Total RNA was isolated from cells with guanidium isothiocyanate/phenol/chloroform. 10 µg of RNA was electrophoresed on a 1.0% agarose gel containing 0.66M formaldehyde, transferred to a DURALON-UV membrane, and cross linked with a UV STRATALINKER (STRATAGENE). Blots were prehybridized and hybridized in a solution of 1% bovine serum albumin, 7% (w/v) SDS, 0.5 M sodium phosphate, and 1 mM EDTA at 65° C. Hybridized blots were washed in 0.1% SDS, 1×SSC for 20 minute periods at 50° C. before film exposure. RNA blots were hybridized with $^{32}$P-labelled cDNA probes for human TGF-β1. A probe for β-actin was used to control for sample loading.

Injection of cells into rabbit—New Zealand white rabbits weighing 2.0–2.5 kg were selected as the animal model. After anesthetization with ketamine and roumpun, each rabbit was draped in a sterile manner. The achilles tendon was exposed, and 0.2–0.3 ml of cells with $10^4$, $10^5$ and $10^6$ cells/ml concentrations were injected into the mid-portion of the tendon. Zinc sulfate was added to the drinking water of the rabbits for the expression of transfected DNA. After determining the optimal concentration with achilles tendon experiments, the intraarticular injection was performed. The knee joint was exposed, and partial and complete cartilage defects were made with a knife. The partial defects were made on the hyaline cartilage layer with caution not to expose the subchondral bone. The complete defects were made to expose the subchondral bone after removing all of the hyaline cartilage. After closing the surgical wound, the cells with $10^6$ cells/ml concentration were injected intraarticularly, and zinc sulfate was added to the drinking water.

Histological examination—After harvesting the tendons and knee joints, the specimens were fixed in formalin and decalcified with nitric acid. They were embedded in a paraffin block and cut into 0.8 µm thickness slices. Hematoxilin-eosine, and Safranin-O staining were utilized to observe the regenerated tissue microscopically.

Example II

Results

Figure 1:
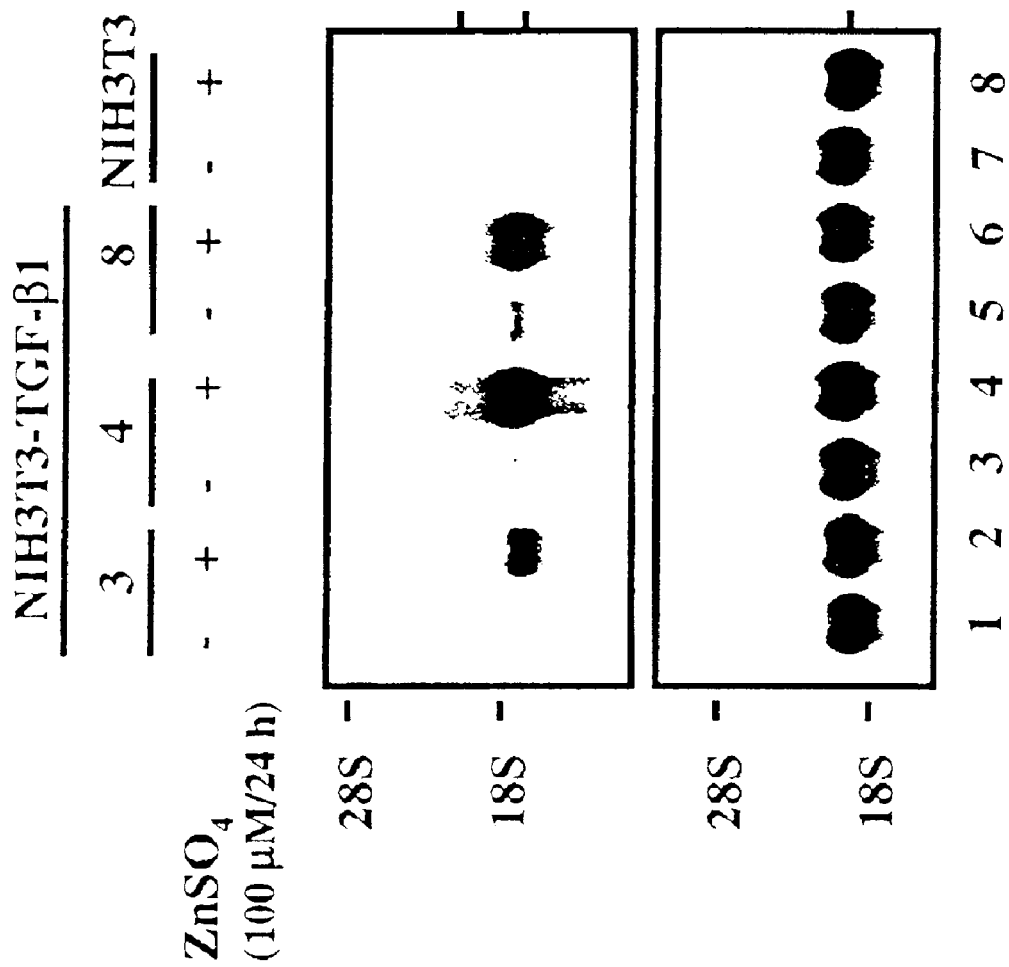
FIG. 1—Expression of TGF-β1 mRNA. Total RNA was isolated from NIH 3T3 cells or NIH 3T3 cells stably transfected with pmTβ1, a TGF-β1 expression vector, which were grown in the absence or presence of zinc. Total RNA (15 mg) was probed with either the TGF-β1 cDNA or β actin cDNA as a control.

Stable cell line—Transfection was carried out by using the calcium phosphate coprecipitation method (FIG. 1). About 80% of the surviving colonies expressed the transgene mRNA. These selected TGF-β1-producing cells were incubated in a zinc sulfate solution. When the cells were cultured in 100 µM zinc sulfate solution, they produced mRNA. The TGF-β secretion rate was about 32 ng/$10^6$ cells/24 hr.

Figure 2:
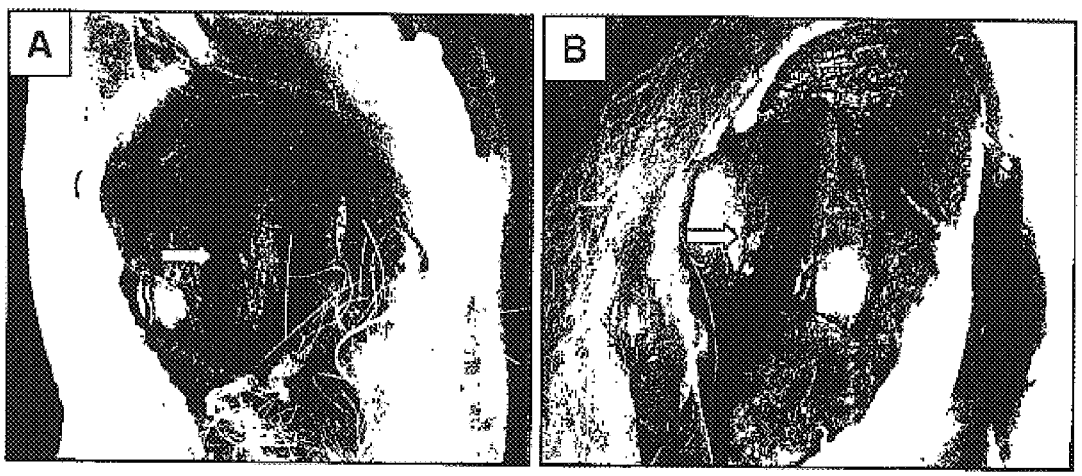
FIGS. 2A–2B—Gross findings of regenerated cartilage.
 2A. A rectangular partial cartilage defect was made on the femoral condyle and the knee joint was injected with NIH 3T3 cells without TGF-β1 transfection. The defect was not covered.
 2B. At 6 weeks after injection of NIH 3T3-TGF-β1 cells, the defect was covered by newly formed tissue. The color of the regenerated tissue was almost identical to that of the surrounding cartilage.
Figure 3:
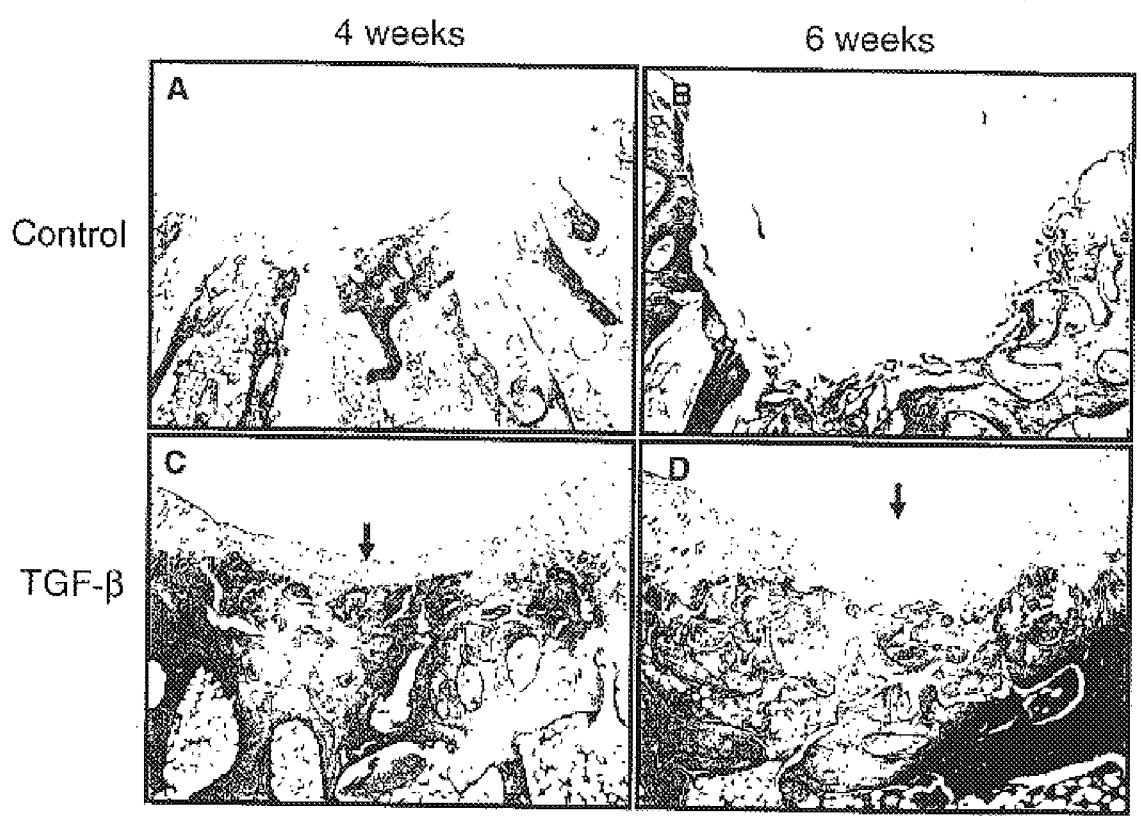
FIGS. 3A–3D—Microscopic findings of regenerated cartilage (×200).
 3A and 3B. Hematoxilin-eosine (H&E) analysis of defect area 4 and 6 weeks after injection with control cells. No tissue covered the initial defect area.
 3C and 3D. Hematoxilin-eosine (H&E) analysis of defect area 4 and 6 weeks after injection of TGF-β1-transfected cells. At 4 weeks, partial defect area was covered by hyaline cartilage after injection of TGF-β1-transfected cells. At 4 weeks and 6 weeks after injection, the regenerated tissue became thicker and its height was almost identical to normal cartilage at 6 weeks. Histologically, the regenerated cartilage (arrow) was identical to the surrounding hyaline cartilage.

Regeneration of Rabbit Articular Cartilage Defect—The rabbit achilles tendons were observed to check the viability of NIH 3T3-TGF-β1 cells. At $10^6$ cells/ml concentration, the tendon was grossly thicker than at the other two concentrations of $10^4$ and $10^5$. After making partial and complete cartilage defects, 0.3 ml of $10^6$ cells/ml of the NIH 3T3-TGF-β1 cells were injected into knee joints. The joint was examined 2 to 6 weeks after injection. In partially damaged cartilage, we found newly formed hyaline cartilage; two weeks after injection, hyaline cartilage appeared and six weeks after injection, the cartilage defects were covered by hyaline cartilage (FIG. 2). The thickness of the regenerated cartilage became thicker as time passed (FIG. 3). The injected cells secreted TGF-β1, that could be observed by immunohistochemical staining with TGF-β1 antibody (FIG. 3). The contralateral side injected with normal fibroblasts without TGF-β1 transfection was not covered by hyaline cartilage. In the partially damaged area, the regenerated hyaline cartilage was colored red in Safranin-O staining (FIG. 4). (The depth of newly formed cartilage was almost the same as that of the defect.) This finding suggests that the injected cells activate the surrounding normal cartilage cells through a paracrine mode of action.

The regenerated tissues in completely damaged cartilage were not hyaline cartilage but fibrous collagen. Their color in Safranin-O staining was white instead of the red color obtained with hyaline cartilage (FIG. 5). The cartilage was covered by fibrous tissue, which means that these cells were activated only by the autocrine mode. The surrounding osteocytes, which can be stimulated by TGF-β, appeared to have been blocked from being stimulated by TGF-β by the presence of a thick calcified bone matrix. The injected cells may have been unable to stimulate the osteocytes because of this barrier.

TGF-β1 transfected cells were injected into rabbit achilles tendon. The tendon so manipulated exhibited a grossly thicker morphology (FIG. 7) than the control tendon. H&E staining of a section of the tendon showed, under microscopic examination, the injected NIH 3T3-TGF-β1 cells survived and produced fibrous collagen in rabbit achilles tendon (FIG. 8). Microscopic examination of the regenerated tendon tissue stained immunohistochemically with TGF-β1 antibody showed the expression of TGF-β1 in the tendon (FIG. 9).

Example III

Either control NIH3T3 or NIH3T3-TGF-β1 cells (5–7× $10^5$) were irradiated with 6000 rad. and injected into rabbit knee joints. These irradiated cells died completely in 3 weeks in a tissue culture dish. The injection procedure was the same as in the previous protocol with untreated cells. The knee joints were harvested at 3 or 6 weeks post injection. The specimens were fixed in formalin and decalcified with nitric acid. Sections of the specimens were made and embedded with paraffin and then cut into 0.5 μm thickness slices. In FIG. 10, Safranin-O staining (A–D & A'–D') and Hematoxilin-Eosine staining (E–F & E'–F') were done in the sections to observe the regenerated cartilage tissue microscopically. (Original magnification: (A, B, A'& B')×12.5; (C–F & C'–F–)×400).

Example IV

Either control human foreskin fibroblast (hFSF) or hFSF-TGF-β1 cells were injected into the rabbit knee joint containing a partial cartilage defect (3mm×5 mm, 1.5 mm deep) on the femoral condyle. These cells (0.5 ml of 2×10$^6$ cells/ml) were injected as in the previous protocol, or 20–25 μl cells of the same concentration were loaded to the top of the defect. In the latter case, the cells were left in the defect for 15–20 min to let them settle down at the bottom of the defect before suturing. In both cases, a similar level of cartilage regeneration was obtained. The specimens were harvested at 6 weeks after injection and observed microscopically. FIGS. 11A & B show pictures of the femoral condyles 6 weeks post injection with either hFSF (A) or hFSF-TGF-β1 cells (B). C, E, & G show Safranin-O staining (C & E) and H&E staining (G) of sections from the femoral condyle injected with control hFSF cells. D, F, & H show Safranin-O staining (D & F) and H&E staining (H) of sections from the femoral condyle injected with hFSF-TGF-β1 cells. (Original magnification: (C & D)×12.5; (E–H)× 400).

Example V

Either control NIH3T3 or NIH3T3-TGF-β1 cells was injected into the dog knee joint containing a partial cartilage defect (6 mm×6 mm, 2 mm deep) on the femoral condyle. These cells (4 ml of 2×10$^6$ cells/ml) were injected as in the previous protocol, or 30–35 μl cells of the same concentration were loaded to the top of the defect. In the latter case, the cells were left in the defect for 15–20 min to let them settle down at the bottom of the defect before suturing. In both cases, a similar level of cartilage regeneration was obtained. The specimens were harvested at 6 weeks post injection and observed microscopically. FIGS. 12, A & B show pictures of the femoral condyles 6 weeks post injection with either NIH3T3 cells (A) or NIH3T3-TGF-β1 cells (B). C, E, & G show Safranin-O staining (C & E) and H&E staining (G) of sections from the femoral condyle injected with control NIH3T3 cells. D, F, & H show Safranin-O staining (D & F) and H&E staining (H) of sections from the femoral condyle injected with NIH3T3-TGF-β1 cells. (Original magnification: (C & D)×12.5; (E–H)×400.)

Whereas particular embodiments of this invention have been described above for purposes of illustration, it will be evident to those persons skilled in the art that numerous variations of the details of the present invention may be made without departing from the invention as defined in the appended claims.

All of the references cited herein are incorporated by reference in their entirety.

References

Andrew J G, Hoyland J, Andrew S M, Freemont A J and Marsh D: Demonstration of TGF-β1 m-RNA by in situ hybridization in normal fracture healing. Calcif Tissue Int, 52: 74–78,1993.

Bourque W T, Gross M and Hall B K: Expression of four growth factors during fracture repair. Int J Dev Biol, 37: 573–579, 1993.

Brand T and Schneider MD: Inactive type II and type I receptors: TGF-β are dominant inhibitors of TGF-β dependent transcription. J Biol Chem, 270: 8274–8284, 1995.

Brittberg M, Lindahl A, Nilsson A. Ohlsson C, Isaksson O and Peterson L: Treatment of deep cartilage defects in the knee with autologous chondrocyte transplantation. New Engl J Med 331: 889–895,1994.

Carrington J L, Roberts A B, Flanders K C, Roche N S and Reddi A H: Accumulation, localization and compartmentation of TGF-β during enchondral bone development J Cell Biology, 107: 1969–1975, 1988.

Centrella M, Massague J and Canalis E: Human platelet-derived transforming growth factor-β stimulates parameters of bone growth in fetal rat calvariae. Endocrinology, 119: 2306–2312, 1986.

Cheifetz S, Weatherbee J A, Tsang M L S, Anderson J K, Lucas R, Massague J: Transforming growth factor beta system, a complex pattern of cross-reactive ligands and receptors. Cell, 48: 409–415,1987.

Chenu C, Pfeilschifter J, Mundy G R and Roodman G D: TGF-β inhibits formation of osteoclast-like cells in long-term human marrow cultures. Proc Natl Acad Sci, 85: 5683–5687, 1988.

Critchlow M A, Bland Y S and Ashhurst D E: The effect of exogenous transforming growth factor-β2 on healing fractures in the rabbit. Bone, 521–527, 1995.

Dallas S L, Miyazono K, Skerry T M, Mundy G R and Bonewald L F: Dual role for the latent transforming growth factor beta binding protein (LTBP) in storage of latent TGF-β in the extracellular matrix and as a structural matrix protein. J Cell Biol, 131: 539–549,1995.

Dumont N, O'Connor M and Philip A: Transforming growth factor receptors on human endometrial cells: identification of the type I and II receptors and glycosyl-phosphatidylinositol anchored TGF-β binding proteins. M Cell Endo, 111: 57–66,1995.

Frenkel S R, Toolan B, Menche D, Pitman M I and Pachence J M: Chondrocyte transplantation using a collagen bilayer matrix for cartilage repair. J Bone J Surg [Br] 79-B: 831–836, 1997.

Heine U I, Munoz E F, Flanders K C, Ellingsworth L R, Peter Lam H-Y, Thompson NL,Roberts A B and Sporn M B: Role of Transforming Growth Factor-β in the development of the mouse embryo. J Cell Biology, 105: 2861–2876, 1987.

Jenks S: Gene therapy: mastering the basics, defining details [news]. J Natl Cancer Inst, 89(16): 1182–1184, 1997.

Joyce M E, Roberts A B, Sporn M B and Bolander M E: Transforming Growth Factor-β and the initiation of chondrogenesis and osteogenesis in the rat femur. J Cell Biology, 110: 2195–2207, 1990.

Lind M, Schumacker B, Soballe K, Keller J, Melsen F, and Bunger: Transforming growth factor-β enhances fracture healing in rabbit tibiae. A Orthop Scand, 64(5): 553–556, 1993.

Lopez-Casillas F, Chifetz S, Doody J, Andres J L, Lane W S Massague J: Structure and expression of the membrane proteoglycan component of the TGF-β receptor system. Cell, 67: 785–795, 1991.

Madri J A, Pratt B M and Tucker A M: Phenotypic modulation of endothelial cells by Transforming Growth Factor-β depends upon the composition and organization of the extracellular matrix. J Cell Biology, 106: 1375–1384, 1988.

Mankin H J: The response of articular cartilage to mechanical injury. J Bone Joint Surg, 52A: 460–466,1982.

Massague, Ann. Rev. Biochem. 67:753–791, 1998.

Matsumoto K, Matsunaga S, Imamura T, Ishidou Y, Yosida H Sakou T: Expression and distribution of transforming growth factors during fracture healing. In vivo, 8: 215–220, 1994.

Miettinen P J, Ebner R, Lopez A R and Derynck R: TGF-β induced transdifferentiation of mammary epithelial cells to mesenchyrnal cells: involvement of type I receptors. J Cell Biology, 127-6:2021–2036, 1994.

O'Driscoll, J. Bone Joint Surg., 80A: 1795–1812, 1998.

Özkaynak E, Rueger D C, Drier E A, Corbett C and Ridge R J: OP-1 cDNA encodes an osteogenic protein in the TGF-β family. EMBO J, 9: 2085–2093, 1990.

Rosenburg L: Chemical basis for the histological use of Safranin-O in the study of articular cartilage. J Bone Joint Surg, 53A: 69–82, 1971.

Sampath T K, Rueger D C: Structure, function and orthopedic applications of osteogenic protein-1 (OP-1). Complications in Ortho, 101–107, 1994.

Snyder S H: The molecular basis of communication between cells. Sci Am, 253(4): 132–140, 1985.

Sporn M B and Roberts A B: Peptide growth factors are multifunctional. Nature (London), 332: 217–219, 1988.

Wakefield L M, Smith D M, Flanders K C and Sporn M B: Latent transforming growth factor-β from human platelets. J Biol Chem, 263, 7646–7654, 1988.

Wolff J A and Lederberg J: A history of gene transfer and therapy. John A. Wolff, Editor. Gene Therapeutics, Mar. 25, 1994. Birkhauser, Boston.

Wrana J L, Attisano L, Wieser R, Ventura F and Massague J: Mechanism of activation of the TGF-β receptor. Nature, 370: 341–347, 1994.

We claim:

1. A method of generating hyaline cartilage, comprising:
   a) generating a recombinant viral or plasmid vector comprising a DNA sequence encoding transforming growth factor β1 (TGF-β1) operatively linked to a promoter;
   b) transfecting in vitro a population of chondrocytes with said recombinant vector, resulting in a population of transfected chondrocytes; and
   c) injecting a composition consisting of the transfected population of chondrocytes and a pharmaceutically acceptable carrier into a joint space of a mammal such that expression of the DNA sequence encoding TGFβ1 within the joint space occurs resulting in the generation of hyaline cartilage in the joint space.

2. The method of claim 1, wherein said recombinant vector is a viral vector.

3. The method of claim 2, wherein said viral vector is retroviral vector.

4. The method of claim 2, wherein said viral vector is adeno-associated viral vector.

5. The method of claim 2, wherein said viral vector is adenoviral vector.

6. The method of claim 2, wherein said viral vector is herpes simplex viral vector.

7. The method of claim 1, wherein said recombinant vector is a plasmid vector.

8. The method of claim 7, wherein said plasmid is pmTβ1.

9. The method of claim 1, wherein said population of transfected chondrocytes are stored prior to injecting the composition.

10. The method of claim 9, wherein said population of transfected chondrocytes are stored in 10% DMSO under liquid nitrogen prior to transplantation.

11. The method of claim 1, wherein in step b), said transfecting is accomplished by liposome encapsulation, calcium phosphate coprecipitation, elcotroporation or DEAE-dextran mediation.

* * * * *